United States Patent [19]

Aller et al.

[11] E Re. 30,240

[45] Reissued Mar. 25, 1980

[54] ARTHROPODICIDAL AND NEMATOCIDAL PHOSPHORAMIDATES

[75] Inventors: Harold E. Aller, Morristown; Edward E. Kilbourn, Chalfont; Ernest D. Weiler, Ambler; William D. Weir, Levittown, all of Pa.

[73] Assignee: Rohm and Haas Company, Philadelphia, Pa.

[21] Appl. No.: 1,800

[22] Filed: Jan. 8, 1979

Related U.S. Patent Documents

Reissue of:

[64] Patent No.: 4,087,521
Issued: May 2, 1978
Appl. No.: 662,743
Filed: Mar. 1, 1976

[51] Int. Cl.[2] ..... A01N 9/36; C07F 9/24

[52] U.S. Cl. ..... 424/211; 260/938

[58] Field of Search ..... 260/938; 424/211

[56] References Cited

U.S. PATENT DOCUMENTS

| | | | |
|---|---|---|---|
| 3,393,253 | 7/1968 | Wiesboeck | 260/938 |
| 3,476,837 | 11/1969 | Addor | 260/959 |
| 3,887,657 | 6/1975 | Battershell et al. | 260/938 |
| 3,957,924 | 5/1976 | Meyer et al. | 260/938 |
| 3,975,522 | 8/1976 | Bader | 260/945 |
| 4,139,614 | 2/1979 | Kilbourn et al. | 424/211 |

FOREIGN PATENT DOCUMENTS

| | | | |
|---|---|---|---|
| 952712 | 11/1956 | Fed. Rep. of Germany | 260/938 |
| 1139494 | 11/1962 | Fed. Rep. of Germany | 260/938 |
| 2114885 | 10/1972 | Fed. Rep. of Germany | 260/938 |
| 2260719 | 6/1974 | Fed. Rep. of Germany | 260/943 |
| 39-18119 | of 1964 | Japan | 260/938 |
| 216712 | 7/1968 | U.S.S.R. | 260/938 |

OTHER PUBLICATIONS

Abstract of Netherlands Patent 7216946 has one earlier application in Switzerland, same as U.S. Pat. No. 3,975,522, Amidines, pp. 405–408.

Abstract of British Patent No. 1,048,314.

*Primary Examiner*—Anton H. Sutto

[57] ABSTRACT

This invention relates to novel phosphoramidates of the formula:

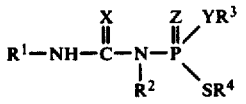

wherein $R^1$ is ($C_6$–$C_{10}$) aryl optionally substituted with alkyl, alkoxy, alkylthio, alkylsulfinyl, alkylsulfonyl, dialkylamino, haloalkyl, hydroxyalkyl, cyano, nitro, hydroxy, or halogen;

$R^2$ is hydrogen[, alkyl, cycloalkyl, alkenyl, or optionally substituted aralkyl or aryl]

$R^3$ is ($C_1$–$C_6$) alkyl;

$R^4$ is ($C_3$–$C_4$) alkyl; *X is sulfur;* and

[X,] Y and Z are independently oxygen or sulfur;

and the agronomically acceptable metal salts and metal salt complexes thereof; to compositions containing them; and to methods of using them to control certain harmful pests, e.g. arthropods and nematodes.

10 Claims, No Drawings

ARTHROPODICIDAL AND NEMATOCIDAL PHOSPHORAMIDATES

Matter enclosed in heavy brackets [ ] appears in the original patent but forms no part of this reissue specification; matter printed in italics indicates the additions made by reissue.

This invention relates to novel phosphoramidates, to compositions containing them, and to methods of using them to control certain harmful pests.

The novel compounds of this invention can be represented by the formula:

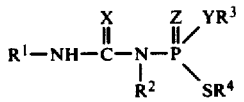

(I)

wherein $R^1$ is a ($C_6$–$C_{10}$) aryl, preferably phenyl, group, optionally substituted with up to five, but preferably up to three, ($C_1$–$C_4$) alkyl groups, ($C_1$–$C_4$) alkoxy groups, ($C_1$–$C_4$) alkylthio groups, ($C_1$–$C_4$) alkylsulfinyl groups, ($C_1$–$C_4$) alkylsulfonyl groups, di-($C_1$–$C_4$) alkylamino groups, ($C_1$–$C_4$) haloalkyl groups, ($C_1$–$C_4$) hydroxyalkyl groups, cyano groups, nitro groups, hydroxyl groups, or halogen atoms;

$R^2$ is

[(a)] a hydrogen atom;

[(b) a ($C_1$–$C_{10}$) alkyl group, preferably a ($C_1$–$C_4$) alkyl group]

[(c) a ($C_3$–$C_8$) cycloalkyl group, preferably a ($C_5$–$C_7$) cycloalkyl group]

[(d) a ($C_3$–$C_6$) alkenyl group, preferably a ($C_3$–$C_4$) alkylenyl group]

[(e) an optionally substituted aralkyl group of up to 11 carbon atoms, preferably an unsubstituted benzyl group; or]

[(f) an optionally substituted ($C_6$–$C_{10}$) aryl group, preferably an unsubstituted phenyl group]

$R^3$ is a ($C_1$–$C_6$) alkyl group, preferably a ($C_1$–$C_4$) alkyl group;

$R^4$ is a ($C_3$–$C_4$) alkyl group;

X is [an oxygen or] *a* sulfur atom;

Y is an oxygen or sulfur atom, preferably an oxygen atom; and

Z is an oxygen or sulfur atom, preferably an oxygen atom;

and the agronomically acceptable metal salts and metal salts complexes thereof.

The metal salts of this invention are the alkali and alkaline earth metal salts of the compounds of Formula I. The preferred metal salt is the sodium salt.

The metal salt complexes of this invention are represented by the following formula which is presented for illustrative purposes only:

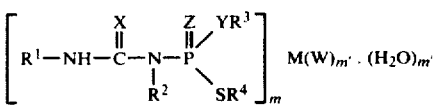

(II)

wherein $R^1$, $R^2$, $R^3$, $R^4$, X, Y, and Z are as defined for Formula I;

M is a metal cation which can be selected from groups IIA, IIA, IB, IIB, VIIB, and VIII of the periodic table;

W is an anion such as chloride, bromide, iodide, sulfate, bisulfate, phosphate, nitrate, perchlorate, carbonate, bicarbonate, hydroxide, acetate, oxalate, malate, citrate, and the like;

m is an integer of 1–2;

m′ is an integer of 1–2; and m″ is an integer of 0–4.

Among the compounds depicted by Formula II above, the preferred compounds are those wherein the metal cation is a transition metal such as copper, zinc, nickel, cobalt, tin, cadmium, or manganese; or an alkaline earth metal such as calcium or magnesium, and wherein the anion is chloride, bromide, nitrate, sulfate or hydroxide. The most preferred salts are those wherein the metal cation is copper, zinc, nickel, cobalt, tin, cadmium or manganese, and the anion is hydroxide.

In Formulas I and II above, $R^2$ is preferably a hydrogen atom.

The preferred compounds of this invention possess especially enhanced nematocidal and arthropodicidal (e.g. acaricidal and insecticidal) activity, and can be represented by the formula:

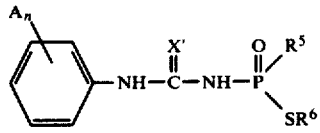

(III)

wherein

A is independently:

(a) a ($C_1$–$C_4$) alkyl group, preferably a methyl group;

(b) a ($C_1$–$C_4$) alkoxy group, preferably a methoxy group;

(c) a ($C_1$–$C_4$) alkylthio group, preferably a methylthio group;

(d) a di-($C_1$–$C_4$) alkylamino group, preferably a dimethylamino group;

(e) a trihalomethyl group, preferably a trifluoromethyl group; or (f) a halogen atom, preferably a chlorine atom;

$R^5$ is a ($C_1$–$C_4$) alkylthio group, preferably a propylthio group, or a ($C_1$–$C_4$) alkoxy group, preferably an ethoxy group;

$R^6$ is a ($C_3$–$C_4$) alkyl group, preferably a n-propyl group, an isobutyl group, or a sec-butyl group;

X′ is [an oxygen or] *a* sulfur atom, preferably an oxygen atom; and n is an integer from 0 to 3, preferably from 0 to 2;

and the agronomically acceptable metal salts and metal salt complexes thereof;

Among the preferred compounds, the most preferred are compounds wherein $R^5$ is an ethoxy group and $R^6$ is an isobutyl group or a sec-butyl group.

As used in the specification and claims, the terms alkyl, alkenyl, alkoxy, alkylthio, alkylsulfinyl, alkylsulfonyl, haloalkyl, hydroxyalkyl, dialkylamino, and aralkyl, are meant to include branched as well as straight chain groups.

Representative $R^1$ substituents include, for example, phenyl, 2-chlorophenyl, 3,4-dichlorophenyl, 2,4,6-trichlorophenyl, 4-bromophenyl, 4-bromo-2-chlorophenyl, 4-fluorophenyl, 3-trifluoromethylphenyl, 4-chloroethylphenyl, 2,4-dimethylphenyl, 2,5-dimethylphenyl, 2-chloro-4-methylphenyl, 2,4-dichloro-3,5-dimethylphenyl, 2-ethyl-4-methoxyphenyl, 4-butylphenyl, 3-methylthiophenyl, 4-methylsulfinylphenyl, 4-methylsulfonylphenyl, 5-methoxyphenyl, 2-ethoxyphenyl, 4-diethylaminophenyl, 4-nitrophenyl, 2-chloro-4-nitrophenyl, 2-cyanophenyl, 2,4-dihdroxyphenyl, 4-hydroxybutylphenyl, naphthyl, 4,6-dichloronaphthyl, 2-methylnaphthyl, 3-methyl-5-methoxynaphthyl, 3,5-ditrifluoromethylnaphthyl, and the like.

[Representative $R^2$ substituents include, for example, hydrogen, methyl, butyl, isopropyl, hexyl, cyclopentyl, cyclohexyl, allyl, 3-butenyl, 4-methyl-2-pentenyl, phenyl, 4-nitrophenyl, 3,5-dichlorophenyl, benzyl, 3,5-dimethylbenzyl, 4-chlorobenzyl, phenethyl, α-methylbenzyl, naphthyl, 3-methylnaphthyl, 3,5-dichloronaphthyl, and the like.]

Representative $R^3$ substituents include, for example, methyl, ethyl, propyl, isopropyl, butyl, isobutyl, sec-butyl, neopentyl, pentyl, hexyl, and the like.

Examples of the compounds embraced by this invention include:

S-(1-methylpropyl) N-phenylaminothiocarbonyl O-propyl phosphoramidothioate

[O,S-dipropyl N-methyl N-phenylaminothiocarbonyl phosphoramidothioate]

[O-butyl S-(2-methylpropyl) N-phenyl N-phenylaminothiocarbonyl phosphoramidothioate]

O-ethyl N-(2-methylphenyl)aminothiocarbonyl S-(1-methylpropyl) phosphoramidothioate O-ethyl N-(4-methoxyphenyl)aminothiocarbonyl S-methylethyl phosphoramidothioate O-ethyl S-(1-methoxypropyl) N-(2-methylthiophenyl)aminothiocarbonyl phosphoramidothioate O-ethyl S-(2-methylpropyl) N-(4-methylsulfonylphenyl)aminothiocarbonyl phosphoramidothioate O-ethyl S-(1-methylpropyl) N-(4-ethylsulfinylphenyl)aminothiocarbonyl phosphoramidothioate O-ethyl N-(3-methyl-4-methylthiophenyl)aminothiocarbonyl S-(1-methylpropyl) phosphoramidothioate

[N-allyl O-ethyl S-(1-methylpropyl) N-(4-nitrophenyl)aminothiocarbonyl phosphoramidothioate]

N-(4-cyanophenyl)aminothiocarbonyl O-ethyl S-(1-methylpropyl) phosphoramidothioate N-(4-diethylaminophenyl)aminothiocarbonyl O-ethyl S-(1-methylpropyl) phosphoramidothioate N-(3,5-dibromophenyl)aminothiocarbonyl O-ethyl S-propyl phosphoramidothioate

[N-(3,5-dichlorophenyl)aminothiocarbonyl O-ethyl N-(4-methylbenzyl) S-(1-methylpropyl) phosphoramidothioate]

N-(2-bromo-4-chlorophenyl)aminothiocarbonyl O-ethyl S-methylethyl phosphoramidothioate S-butyl N-(3,5-dichlorophenyl)aminothiocarbonyl O-ethyl phosphoramidothioate N-(2,4-dichlorophenyl)aminothiocarbonyl O-methyl S-(1-methylpropyl) phosphoramidothioate N-(3,4-dichlorophenyl)aminothiocarbonyl O-hexyl S-(1-methylpropyl) phosphoramidothioate N-(3,5-dichlorophenyl)aminothiocarbonyl S,S-dipropyl phosphoramidodithioate N-(2,4-dichlorophenyl)aminothiocarbonyl S,S-bis-(1methylpropyl) phosphoramidotrithioate O-ethyl S-(1-methylpropyl) N-(2,4,6-trichlorophenyl)aminothiocarbonyl phosphoramidothioate N-(3,5-ditrifluoromethylphenyl)aminothiocarbonyl O-ethyl S-(2-methylpropyl) phosphoramidothioate O-ethyl N-(2-hydroxyphenyl)aminothiocarbonyl S-(1-methylpropyl) phosphoramidothioate O-ethyl N-(2-hydroxymethylphenyl)aminothiocarbonyl S-(1-methylpropyl) phosphoramidothioate O-ethyl S-(1-methylpropyl) N-(2-naphthyl)aminothiocarbonyl phosphoramidothioate O-ethyl S-methylethyl N-[1-(3-trifluoromethyl)naphthyl]aminothiocarbonyl phosphoramidothioate

[O-ethyl S-methylpropyl) N-phenylaminocarbonyl phosphoramidothioate]

[N-benzyl O-ethyl S-(1-methylpropyl) N-phenylaminocarbonyl phosphoramidothioate]

[S,S-dipropyl N-phenylaminocarbonyl phosphoramidothioate]

[N-(2,4-dimethylphenyl)aminocarbonyl O-ethyl S-(1-methylpropyl) phosphoramidothioate]

[O-ethyl S-(1-methylpropyl) N-(4-propylthiophenyl)aminocarbonyl phosphoramidothioate]

[N-(3,4-dichlorophenyl)aminocarbonyl S,S-dipropyl phosphoramidotrithioate]

[N-(2,4-dichlorophenyl)aminocarbonyl S-ethyl N-methylethyl S-propyl phosphoramidodithioate]

[N-(2,3,4,5,6-pentachlorophenyl)aminocarbonyl O-ethyl S-propyl phosphoramidothioate]

[O-ethyl N-(4-fluorophenyl)aminocarbonyl S-propyl phosphoramidothioate]

[N-(4-chloro-2-methylphenyl)aminocarbonyl O-ethyl S-(1-methylpropyl) phosphoramidothioate]

[N-(4-chloromethylphenyl)aminocarbonyl S-(1-methylpropyl) O-propyl phosphoramidothioate]

[N-(2-butenyl) N-3,5-ditrifluoromethylphenyl-)aminocarbonyl O-ethyl S-propyl phosphoramidothioate]

[N-(4-cyano-2-nitrophenyl)aminocarbonyl O-ethyl S-(1-methylpropyl) phosphoramidothioate]

[N-(4-chlorophenyl)aminocarbonyl N-(4-cyanophenyl) O-ethyl S-(1-methylpropyl) phosphoramidothioate]

[O-ethyl S-(1-methylpropyl) N-(2-naphthyl-)aminocarbonyl phosphoramidothioate]

[S,S-dipropyl N-(1-naphthyl)aminocarbonyl phosphoramidodithioate]

[N-[1-(5,7-dichloronaphthyl)aminocarbonyl] O-ethyl S-(2-methylpropyl) phosphoramidothioate]

[S-butyl O-methyl N-[1-(3-methylnaphthyl-)aminocarbonyl] phosphoramidothioate]

[N-[2-(5,7-dinitronaphthyl)aminocarbonyl] O-ethyl S-propyl phosphoramidothioate]

and the agronomically acceptable metal salts and metal salt complexes thereof, and the like.

The phosphoramidates of this invention are prepared by various methods. One method involves contacting an appropriate aromatic amine with an appropriately substituted phosphoroisothiocyanate or phosphoroisocyanate. This reaction can be represented by the following equation:

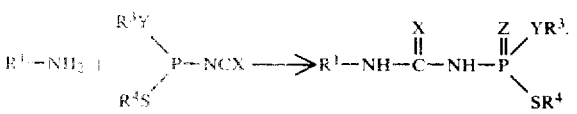

wherein $R^1$, $R^3$, $R^4$, X, Y, and Z are as defined for Formula I.

The reaction is generally carried out in the presence of an aprotic solvent such as glyme, acetone, acetonitrile, ethyl acetate, butyl acetate, diethyl ether, or mixtures thereof, at a temperature range of about 15° to about 120° C., preferably at about 25° to about 45° C. A substantially equimolar ratio of reactants is preferred, but an excess of phosphoroisothiocyanate or isocyanate can be used. The desired product can be separated from the reaction mixture by conventional means, such as fractional crystallization, chromatography, extraction or the like.

[Another method for preparing compounds within the scope of this invention involves contacting an appropriate aromatic amine with an appropriately substituted chloro(thio)carbonyl phosphoramidate. This reaction can be represented by the following equation:]

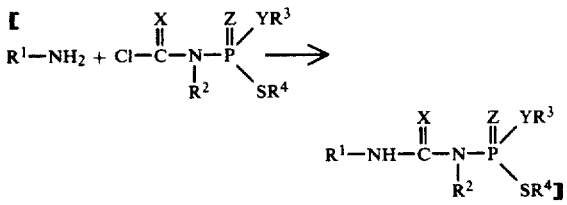

[wherein $R^1$, $R^2$, $R^3$, $R^4$, X, Y, and Z are as defined for Formula I, with the exception that $R^2$ may not be hydrogen.]

[This reaction is generally carried out in the presence of an aprotic solvent such as glyme, acetone, acetonitrile, ethyl acetate, butyl acetate, diethyl ether, or mixtures thereof, at a temperature range of about 15° to about 120° C., preferably at about 25° to about 45° C. An acid acceptor such as a tertiary amine can be employed as a scavenger in this preparation. Representative acid acceptors include pyridine, trimethylamine, triethylamine, and the like. However, an excess of the amine reactant can also serve as the acid acceptor. Generally, a substantially equimolar ratio of reactants is preferred, but an excess of two or more moles of amine can be employed if the amine is intended to serve the dual function of reactant and acid acceptor. The desired product can be separated from this reaction mixture by conventional means.]

[A third] *Another* method of preparing compounds of this invention involves contacting an appropriate phosphoramidate with an appropriate isocyanate or isothiocyanate. This reaction can be represented by the following equation:

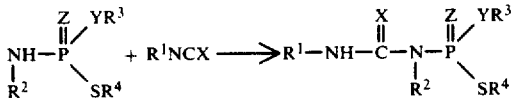

wherein $R^1$, $R^2$, $R^3$, $R^4$, X, Y, and Z are as defined for Formula I.

The reaction is generally carried out in the presence of an aprotic solvent such as glyme, acetone, acetonitrile, ethyl acetate, butyl acetate, diethyl ether, or mixtures thereof, at a temperature range of about 20° to about 60° C., room temperature being preferred. A substantially equimolar ratio of reactants is preferred. The desired product can be separated from the reaction mixture by conventional means.

The metal salts of this invention are prepared by (1) adding an alkali or alkaline earth metal hydroxide or hydride to a suspension of the phosphoramidate in a suitable solvent, (2) stirring the mixture until a solution forms, and (3) freeze drying the solution, or in the alternative, (4) concentrating the solution in vacuo at room temperature, and drying the residue in a vacuum oven at room temperature.

The metal salt complexes are prepared by (1) reacting, in an aqueous or alcoholic medium, a phosphoramidate of this invention, with a metal salt selected from group IIA, IIIA, IB, IIB, VIIB, or VIII of the periodic table, (2) filtering off the precipitate which forms, and (3) washing and drying the precipitate to give the product.

All of the starting materials used in the preparation of the compounds of this invention are known compounds or are readily prepared by methods available to those skilled in the art.

By way of demonstration, the following examples are offered to illustrate this invention and are not to be construed as limitations thereof.

[EXAMPLE 1]

[Preparation of O-ethyl S-(1-methylpropyl) N-phenylaminocarbonyl phosphoramidothioate]

[To a solution of 0.93 g. (0.01 mole) of aniline in 5 ml. of glyme is added 2.23 g. (0.01 mole) of O-ethyl S-(1-methylpropyl) phosphoroisocyanatothioate (exothermic reaction). The solution is allowed to stand at room temperature from 24 hours and then poured into 250 ml. of water. The semi-solid precipitate is isolated and slurried in 20 ml. of ether. The ethereal slurry is filtered and dried to afford 0.35 g. (11%) of product.]

EXAMPLE 6

Preparation of O-ethyl N-(4-methylphenyl) aminothiocarbonyl S-(1-methylpropyl) phosphoramidothioate To a solution of 1.07 g. (0.01 mole) of 4-methylaniline in 5 ml. of glyme is added 2.39 g. (0.01 mole) of O-ethyl S-(1-methylpropyl) phosphoroisocyanatothioate (exothermic reaction). The solution is allowed to stand at room temperature for six days and then poured into an excess of water (300 ml.). The suspension which forms is vacuum filtered. The filter cake is slurried in 50 ml. of hexane, filtered, and dried to afford 1.6 g. (47%) of product.

EXAMPLE 9

Preparation of O-ethyl N-(4-methylphenyl)aminothiocarbonyl S-(1-methylpropyl) phosphoramidothioate To a solution of 1.23 g. (0.01 mole) of 4-methoxyaniline in 5 ml. of glyme is added 2.39 g. (0.01 mole) of O-ethyl S-(1-methylpropyl) phosphoroisothiocyanatothioate (exothermic reaction). The solution is allowed to stand at room temperature for 18 hours and then poured into an excess of water. The suspension which forms is vacuum filtered and the filter cake is slurried in 100 ml. of hexane, filtered, and dried to afford 2.4 g. (66.5%) of product.

EXAMPLE 10

Preparation of
N-(4-dimethylaminophenyl)aminothiocarbonyl O-ethyl S-(1-methylpropyl) phosphoramidothioate To a solution of 1.36 g. (0.01 mole) of N,N-dimethyl-4-phenylenediamine in 5 ml. of glyme is added 2.39 g. (0.01 mole) of O-ethyl S-(1-methylpropyl) phosphoroisothiocyanatothioate (exothermic reaction). The solution is allowed to stand at room temperature for 24 hours and then poured into an excess of water. The precipitate which forms is slurried in hexane and then vacuum filtered. The filter cake is re-slurried in 15 ml. of ethyl acetate, vacuum filtered and dried to afford 0.9 g. (24.6%) of product.

EXAMPLE 14

Preparation of
N-(3,5-dichlorophenyl)aminothiocarbonyl O-ethyl S-propyl phosphoramidothioate To a solution of 1.62 g. (0.01 mole) of 3,5-dichloroaniline in 5 ml. of glyme is added 2.25 g. (0.01 mole) of O-ethyl S-propyl phosphoroisothiocyanatothioate. The product is obtained by pouring the reaction solution into an excess of water, vacuum filtering the suspension which forms, and recrystallizing the isolated precipitate from methylcyclohexane. The yield of product is 1.8 g. (47.5%).

EXAMPLE 15

Preparation of
N-(3,5-dichlorophenyl)aminothiocarbonyl O-ethyl S-methylethyl phosphoramidothioate To a solution of 2.82 g. (0.0178 mole) of 3,5-dichloroaniline in 5 ml. of glyme is added 4 g. (0.0178 mole) of O-ethyl S-methylethyl phosphoroisothiocyanatothioate. The solution is heated to reflux and is allowed to stand at room temperature for two hours. The suspension which forms is vacuum filtered. The filter cake is washed with 10 ml. of glyme, 20 ml. of ether, and dried to afford 2 g. (29%) yield of product.

EXAMPLE 17

Preparation of
N-(3,5-dichlorophenyl)aminothiocarbonyl O-ethyl S-(2-methylpropyl) phosphoramidothioate To a solution of 1.62 g. (0.01 mole) of 3,5-dichloroaniline in 5 ml. of glyme is added 2.39 g. (0.01 mole) of O-ethyl S-(2-methylpropyl) phosphoroisothiocyanatothioate. The solution is heated to reflux and allowed to stand at room temperature for three days. The solution is poured into an excess of water and the semi-solid precipitate which forms is isolated. The product is slurried in 50 ml. of hexane and vacuum filtered. The filter cake is dried to afford 1.8 g. (45%) of product.

EXAMPLE 18

Preparation of
N-(3,5-dichlorophenyl)aminothiocarbonyl O-ethyl S-(1-methylpropyl) phosphoramidothioate To a solution of 3.24 g. (0.02 mole) of 3,5-dichloroaniline in 15 ml. of glyme is added 4.8 g. (0.02 mole) of O-ethyl S-(1-methylpropyl) phosphoroisothiocyanatothioate. The solution is allowed to stand at room temperature for 18 hours and then poured into an excess of water. The semi-solid precipitate which forms is isolated and slurried in 50 ml. of hexane. The hexane slurry is filtered to afford 3.25 g. (40.5%) of product, m.p. 123°-125° C. Recrystallization from methylcyclohexane gives 2.5 g. (31%) of product.

[EXAMPLE 23]

[Preparation of
N-(3,5-ditrifluoromethylphenyl)aminothiocarbonyl O-ethyl S-(1-methylpropyl) phosphoramidothioate To a solution of 1.03 g. (0.0045 mole) of 3,5-ditrifluoromethylaniline in 5 ml. of glyme is added 1 g. (0.0045 mole) of O-ethyl S-(1-methylpropyl) phosphoroisothiocyanatothioate (exothermic reaction). The solution which forms is allowed to stand at room temperature for 1½ hours and is poured into 200 ml of water. The suspension which forms is vacuum filtered and the filter cake recrystallized from methylcyclohexane to afford 0.92 g. (46%) of product.]

TABLE I

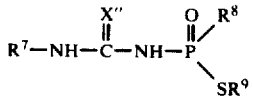

| Compound Number | X'' | $R^7$ | $R^8$ | $R^9$ | M.P., °C. | ELEMENTAL ANALYSIS Calculated (Found) %C | %H | %N | %P | %S |
|---|---|---|---|---|---|---|---|---|---|---|
| [1 | 0 | $C_6H_5$ | $OC_2H_0$ | $C_4H_9^s$ | 74-77 | 49.35 | 6.69 | 8.86 | 9.79 | — |
| | | | | | | (49.22) | (6.84) | (8.64) | (9.60) | —] |
| 2 | S | $C_6H_5$ | $OC_2H_5$ | $C_3H_7^i$ | 9-101 | 45.43 | 5.98 | 8.84 | 9.94 | 19.67 |
| | | | | | | (45.26) | (6.03) | (8.80) | (9.73) | (20.14) |
| [3 | O | $C_6H_4CH_3$-2 | $OC_2H_5$ | $C_4H_9^s$ | oil | 50.8 | 7.0 | 8.5 | — | 9.7 |
| | | | | | | (50.5) | (6.7) | (8.3) | — | (9.6) |
| 4 | O | $C_6H_4CH_3$-4 | $OC_2H_5$ | $C_4H_9^s$ | 75-80 | 51.0 | 6.7 | 8.5 | — | — |
| | | | | | | (50.7) | (7.1) | (.5) | — | — |
| 5 | O | $C_6H_4CH_3$—4 | $OC_2H_5$ | $C_4H_9^s$ | 130-135 | 50.8 | 7.0 | 8.5 | — | 9.7 |
| | | | | | | (50.3) | (6.9) | (8.1) | — | (10.0)] |
| 6 | S | $C_6H_4CH_3$-4 | $OC_2H_5$ | $C_4H_9^s$ | 78-80 dec. | 48.42 | 6.66 | 7.96 | 9.12 | — |
| | | | | | | (48.53) | (6.69) | (8.09) | (8.94) | — |
| [7 | O | $C_6H_4CH_3$-4 | $OC_2H_5$ | $C_4H_9^i$ | 120-122 | 50.9 | 7.0 | 8.5 | — | 9.7 |
| | | | | | | (50.6) | (6.9) | (8.6) | — | (9.9) |
| 8 | O | $C_6H_4SCH_3$-4 | $OC_2H_5$ | $C_4H_9^s$ | 101-104 | 46.07 | 6.60 | 7.57 | 8.78 | 17.80 |
| | | | | | | (46.39) | (6.41) | (7.73) | (8.54) | (17.69)] |
| 9 | S | $C_6H_4OCH_3$-4 | $OC_2H_5$ | $C_4H_9^s$ | 80-83 dec. | 46.00 | 6.23 | 7.41 | 8.46 | — |
| | | | | | | (46.39) | (6.40) | (7.73) | (8.55) | — |

TABLE I-continued

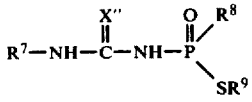

| Compound Number | X'' | $R^7$ | $R^8$ | $R^9$ | M.P., °C. | ELEMENTAL ANALYSIS Calculated (Found) %C | %H | %N | %P | %S |
|---|---|---|---|---|---|---|---|---|---|---|
| 10 | S | $C_6H_4N(CH_3)_2$-4 | $OC_2H_5$ | $C_4H_9^s$ | 99–103 dec. | 48.00 (47.98) | 7.15 (6.98) | 11.20 (11.19) | 8.23 (8.25) | — — |
| [11 | O | $C_6H_4NO_2$-4 | $OC_2H_5$ | $C_4H_9^s$ | 108–112 | 43.3 (43.1) | 5.6 (5.5) | 11.6 (11.6) | — — | —] |
| 12 | S | $C_6H_4Cl$-4 | $OC_2H_5$ | $C_4H_9^s$ | 83–85 | 42.71 (42.56) | 5.59 (5.50) | 7.43 (7.64) | 8.35 (8.44) | — — |
| [13 | O | $C_6H_4Cl$-4 | $OC_2H_5$ | $C_4H_9^s$ | 89–93 dec. | 43.35 (44.51) | 5.74 (5.75) | 7.59 (7.99) | — — | —] |
| 14 | S | $C_6H_2Cl_2$-3,5 | $OC_2H_5$ | $C_3H_7$ | 122–124 | 37.18 (37.21) | 4.54 (4.43) | 7.33 (7.23) | — — | — — |
| 15 | S | $C_6H_3Cl_2$-3,5 | $OC_2H_5$ | $C_3H_7$ | 138.5–141 | 37.35 (37.21) | 4.43 (4.43) | 7.10 (7.23) | 7.98 (8.00) | — — |
| 16 | S | $C_6H_3Cl_2$-3,5 | $OC_2H_5$ | $C_4H_9$ | 93–96 | 38.61 (38.90) | 4.84 (4.77) | 6.86 (6.98) | — — | — — |
| 17 | S | $C_6H_3Cl_2$-3,5 | $OC_2H_5$ | $C_4H_9^i$ | 108–111 | 38.90 (38.90) | 4.70 (4.77) | 6.84 (6.98) | 7.70 (7.72) | — — |
| 18 | S | $C_6H_3Cl_2$-3,5 | $OC_2H_5$ | $C_4H_9^s$ | 130–131 | 39.02 (38.90) | 4.87 (4.77) | 7.08 (6.98) | — — | — — |
| 19 | [O | $C_6H_3Cl_2$-3,5 | $OC_2H_5$ | $C_4H_9^s$ | 144.5–147 dec. | 40.18 (40.53) | 5.06 (4.97) | 6.99 (7.27) | 7.93 (8.04) | —] |
| 20 | S | $C_6H_3Cl_2$—3,5 | $SC_3H_7$ | $C_3H_7$ | 89–91 dec. | 37.21 (37.41) | 4.62 (4.59) | 6.60 (6.71) | 7.42 (7.42) | — — |
| 21 | S | $C_6H_3Cl_2$-2,4 | $OC_2H_5$ | $C_4H_9^s$ | 82–84 | 38.99 (38.90) | 4.81 (4.77) | 6.75 (6.98) | 7.79 (7.72) | — — |
| 22 | S | $C_6H_3(CF_3)_2$-3,5 | $OC_2H_5$ | $C_4H_9^s$ | 125.5–123.5 | 38.16 (38.46) | 4.15 (4.09) | 5.92 (5.98) | 6.54 (6.61) | — — |
| 23 | [O. | $C_6H_3(CF_3)_2$-3,5 | $OC_2H_5$ | $C_4H_9^s$ | 162–164.5 | 40.36 (39.82) | 4.52 (4.23) | 6.19 (6.19) | — — | — — |
| 24 | O | $C_6H_3(CF_1)_2$-3,5 | $OC_2H_5$ | $C_3H_7^i$ | 183–185 | 38.19 (38.86) | 4.20 (3.92) | 6.33 (6.39) | 6.99 (7.06) | 7.52 (7.31)] |
| 25 | S | $C_6H_3(CF_3)_2$—3,5 | $OC_2H_5$ | $C_3H_7^i$ | 127–128 | 37.00 (37.00) | 3.86 (3.78) | 6.00 (6.14) | 6.74 (6.82) | 14.47 (14.11) |

$^i$ = iso
$^s$ = secondary

The present compounds and the metal salts and metal salt complexes thereof (hereinafter collectively referred to as compounds or phosphoramidates) are useful for the protection of plants and animals, including man, from the ravages of harmful and annoying pests. These compounds are particularly effective against nematodes and arthropods in varying stages of development. As arthropodicides, the compounds of this invention are especially effective against members of the class Arachnoidea, which includes the Order Acarina, as represented by mites and ticks, and the class Insecta, the insects. Among the arthropods and nematodes which are effectively controlled by the compounds of the present sent invention are the chewing insects, e.g. the southern arymworm (Spodoptera eridania), the sucking insects, e.g. the green peach aphid (Myzus persicae), soil-dwelling insects, e.g. the southern corn rootworm (Diabrotica undecimpunctata howardi), houseflies, mites, e.g. the two-spotted spider mite (Tetranychus urticae), the southern root knot nematode (Meloidogyne incognita), and others. Certain compounds of this invention are also active as anthelmintics.

Generally, control of pests is achieved in accordance with this invention by application of the compounds of this invention in pesticidally effective amounts (e.g. arthropodically or nematocidally effective amounts) either directly to the pests to be controlled or to the loci to be protected from attack by such pests. For example, food, fiber, forage, forest, and ornamental crops and stored products thereof would represent plant protection loci. Treatment with the compounds of this invention of domestic animals, man and their immediate environs similarly constitute representative loci for protection against various annoying ectolparasitic or endoparasitic Acarina (Acari) and Insecta. Accordingly, compounds of the present invention provide utility as the essential active ingredient of pesticidal compositions suitable for agricultural and sanitary purposes.

The term "control" as employed in the specification and claims of this application is to be construed as any means which adversely effects the existence or growth of any living organism. Such means can comprise a complete killing action, eradication, arresting in growth, repulsion, inhibition, reduction in number, or any combination thereof.

For use as pesticides, the compounds of this invention can be used as solutions, suspensions, or mixtures, in organic solvents or formulations. For example, they can be formulated as wettable powders, emulsifiable concentrates, dusts, granular formulations or flowable emulsifiable concentrates. In such formulations, the phosphoramidates are present at a concentration of about 0.00001 to about 99%, preferably about 1 to about 95%, and are extended with an agronomically acceptable liquid or solid carrier. When desired, suitable surfactants are likewise incorporated. Surfactants commonly used in the art can be found in the John W. McCutcheon, Inc. publication "Detergents and Emulsifiers Annual."

By "agronomically acceptable carrier" is meant any substance which can be utilized to dissolve, disperse or duffuse the chemical incorporated therein without impairing the effectiveness of the toxic agent and which does no permanent damage to such environment as soil, equipment, and agronomic crops.

The phosphoramidate can be taken up on or mixed with a finely particled solid carrier, as for example, clays, inorganic silicates, carbonates, and silicas.

Organic carriers can also be employed. Dust concentrates are commonly made wherein phosphoramidates are present in the range of about 20 to about 80%. For ultimate applications, these concentrates are normally extended with additional solid to give an active ingredient content of from 1 to about 20%. Granular formulations are made using a granular or pelletized form of carrier, such as granular clays, vermiculite, charcoal or corn cobs, and may contain the active ingredient in from about 1 to about 25% by weight.

Wettable powder formulations are made by incorporating the compounds of this invention in an inert, finely divided solid carrier along with a surfactant which can be one or more emulsifying, wetting, dispersing, or spreading agents or a blend of these. The phosphoramidates are usually present in the range of about 10 to about 80% by weight and surfactants in from about 0.5 to about 10% by weight. Commonly used emulsifying and wetting agents include polyoxyethylated derivatives of alkylphenols, fatty alcohols, fatty acids, alkylamines, alkylarene sulfonates and dialkyl sulfosuccinates. Spreading agents include such materials as glycerol mannitan laurate and a condensate of polyglycerol and oleic acid modified with phthalic anhydride. Dispersing agents include such materials as the sodium salt of the copolymer of maleic anhydride and an olefin such as diisobutylene, sodium lignin sulfonate and sodium formaldehydenaphthalene sulfonates.

One convenient method for preparing a solid formulation is to impregnate the phosphoramidate onto the solid carrier by means of a volatile solvent, such as acetone. In this manner, adjuvants, such as activators, adhesives, plant nutrients, synergists and various surfactants can also be incorporated.

Emulsifiable concentrate formulations are prepared by dissolving the phosphoramidates of this invention in an agronomically acceptable organic solvent and adding a solvent soluble emulsifying agent. Suitable solvents are usually water-immersible and can be found in the hydrocarbon, chlorinated hydrocarbon, ketone, ester, alcohol and amide classes of organic solvents. Mixtures of solvents are commonly employed. The surfactants useful as emulsifying agents can constitute about 0.5 to about 10% by weight of emulsifiable concentrates and can be anionic, cationic or non-ionic in character. The concentration of the active ingredients can vary from about 10 to about 80%, preferably in the range of about 25 to about 50%.

For use as pesticidal agents, these compounds should be applied in an effective amount sufficient to exert the desired pesticidal activity by techniques well known in the art. In certain situations, however, it may be desirable and advantageous to apply the phosphoramidate directly onto the loci to be protected or freed of pests without the benefit of any substantial amount of carrier. This is a particularly effective method when the physical nature of the toxicants is such as to permit what is known as "low-volume" application, that is, when the compounds are in liquid form or substantially soluble in higher boiling solvents.

The application rate will, of course, vary depending upon the purposes for such application, the phosphoramidate being utilized, the frequency of dissemination, and the like.

Many of the above formulations can be utilized on animals for the control of parasites.

For use as arthropodicides, e.g. acaricides and insecticides, dilute sprays can be applied at concentrations of about 0.01 to about 20 pounds of the active ingredient per 100 gallons of spray. They are usually applied at about 0.1 to about 5 pounds per 100 gallons. In more concentrated sprays, the active ingredient is increased by a factor of 2 to 40. With dilute sprays, applications are usually made to the plants until run-off is achieved, whereas with more concentrated or low-volume sprays, the materials are applied as mists.

For use as soil insecticides or as nematocides, the phosphoramidates can be applied as a diluted liquid preparation or as a solid formulation, preferably a granular formulation, by broadcasting, side-dressing, introduction into the seed furrow, soil incorporation, or seed treatment. The application rate can be from about 1 to about 50 pounds per acre of active ingredient and for economic reasons, preferably from about 1 to about 25 pounds per acre.

The compounds of this invention can be utilized as the sole pesticidal agents or they can be employed in conjunction with other bactericides, fungicides, herbicides, insecticides, acaricides, and comparable pesticides.

Many variations of this invention are possible without departing from the spirit or scope thereof.

We claim:

1. A method of controlling pests which comprises applying directly to the pests or to the loci to be freed of or protected from attack by such pests, a pesticidally effective amount of a compound of the formula

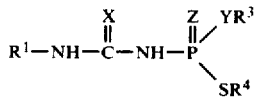

wherein $R^1$ is a ($C_6$–$C_{10}$) aryl group, optionally substituted with up to five ($C_1$–$C_4$) alkyl groups, ($C_1$–$C_4$) alkoxyl groups, ($C_1$–$C_4$) alkylthio groups; ($C_1$–$C_4$) alkylsulfonyl groups, ($C_1$–$C_4$) hydroxyalkyl groups, ($C_1$–$C_4$) haloalkyl groups, cyano groups, nitro groups, hydroxyl groups, or halogen atoms;

$R^3$ is a ($C_1$–$C_6$) alkyl group;

$R^4$ is a ($C_3$–$C_4$) alkyl group;

X is [an oxygen or] *a* sulfur atom;

Y is an oxygen or sulfur atom; and

Z is an oxygen or sulfur atom and the agronomically acceptable metal sales and metal salt complexes thereof.

2. A compound of the formula:

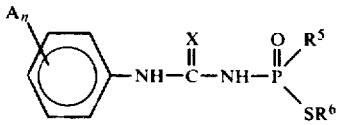

wherein

A is independently (a) a ($C_1$-$C_4$) alkyl group;

(b) a ($C_1$-$C_4$) alkoxy group;

(c) a ($C_1$-$C_4$) alkylthio group;

(d) a trihalomethyl group; or (e) a halogen atom;

$R^5$ is a ($C_1$-$C_4$) alkylthio group or a ($C_1$-$C_4$) alkoxy group;

$R^6$ is a ($C_3$-$C_4$) alkyl group;

X is [an oxygen or] *a* sulfur atom; and n is an integer from 0 to 3 and the agronomically acceptable metal salts and metal salt complexes thereof.

3. A compound according to claim 2 wherein

A is independently (a) a methyl group;

(b) a methoxy group;

(d) a trifluoromethyl group; or (e) a chlorine atom;

$R^5$ is a propylthio group or an ethoxy group;

$R^6$ is a n-propyl, isobutyl, or sec-butyl group;

X' is [an oxygen or] *a* sulfur atom; and n is an integer of 0 to 2.

4. A compound according to claim 3 wherein $R^5$ is an ethoxy group and $R^6$ is an isobutyl group or a sec-butyl group.

[5. A compound according to claim 4 having the formula:

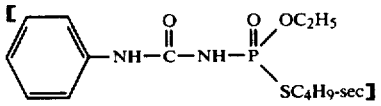

]

[6. A compound according to claim 4 having the formula:

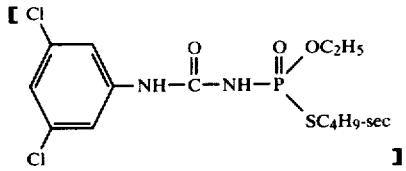

]

7. A compound according to claim 4 having the formula:

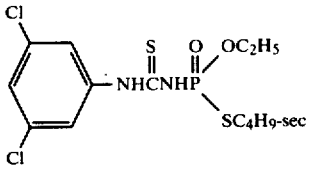

[8. A compound according to claim 5 having the formula:

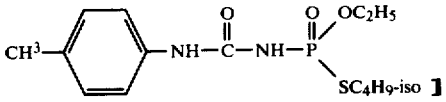

]

[9. A compound according to claim 5 having the formula:

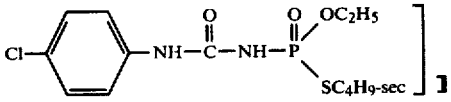

]

10. A pesticidal composition comprising a compound according to claim 1 and an agronomically acceptable carrier.

11. A method of controlling pests which comprises applying directly to the pests or to the loci to be freed of or protected from attack by such pests, a pesticidally effective amount of the composition of claim 10.

12. A method according to claim 11 wherein the pests are arthropods.

13. A method according to claim 12 wherein the arthropods are insects or acarids.

14. A method according to claim 11 wherein the pests are nematodes.

* * * * *